United States Patent [19]

Seely et al.

[11] Patent Number: 5,137,872
[45] Date of Patent: Aug. 11, 1992

[54] GROWTH HORMONE-RELEASING FACTOR ANALOGS

[75] Inventors: James E. Seely; Hsi Meng, both of Terre Haute, Ind.

[73] Assignee: Pitman-Moore, Inc., Lake Forest, Ill.

[21] Appl. No.: 408,728

[22] Filed: Sep. 18, 1989

[51] Int. Cl.$^5$ .................. C07K 7/10; A61K 37/02
[52] U.S. Cl. ........................... 514/12; 514/21; 530/342; 530/399; 424/422; 604/93
[58] Field of Search ............... 530/324, 399; 514/12, 514/21; 424/422; 604/93

[56] References Cited

U.S. PATENT DOCUMENTS

| | | | |
|---|---|---|---|
| 4,659,693 | 4/1987 | Nestor | 514/12 |
| 4,728,726 | 3/1988 | Rivier et al. | 530/324 |
| 4,801,456 | 1/1989 | Drengler | 424/422 |
| 4,833,166 | 5/1989 | Grosvenor et al. | 514/12 |
| 4,839,344 | 6/1989 | Bowers et al. | 514/16 |

OTHER PUBLICATIONS

Frohman et al., Rapid Enzymatic Degradation of Growth Hormone–releasing Hormone by Plasma In Vitro and In Vivo to a Biologically Inactive Product Cleaved at the NH$_2$ Terminus, *J. Clin. Invest.*, vol. 78, pp. 906–913 (1986), Hodate et al., Response of Growth Hormone Release to Human Growth Hormone–Releasing Factor and Its Analogs in the Bovine, *Endocrinol. Japan*, 33 (4) pp. 519–525 (1986).

Karashima et al., Effect of Long-Term Administration of an Analog of Growth Hormone–Releasing Factor on the GH Response in Rats, *Life Sciences*, vol. 40, pp. 2437–2444 (1987).

*Primary Examiner*—F. T. Moezie
*Attorney, Agent, or Firm*—Wendell R. Guffey; Thomas L. Farquer; Barbara G. Ernst

[57] ABSTRACT

Human Growth Hormone-Releasing Factor (hGRF) analogs having the sequence [Pro$^0$, X$^{15}$, Y$^{27}$]-hGRF(1-A)-B, wherein X is selected from the group consisting of Ala and Gly, Y is selected from the group consisting of Ile, Leu, Val, Nle and Met, A has a value from 29–44, and B is NH$_2$, OH or COOH are synthesized and administered to animals to stimulate the release of Growth Hormone (GH).

23 Claims, 2 Drawing Sheets

GROWTH HORMONE-RELEASING FACTOR ANALOGS

This invention relates generally to human growth hormonereleasing factor (hGRF) analogs and particularly to hGRF analogs having the sequence [Pro$^0$, X$^{15}$, Y$^{27}$]-hGRF(1-A)-B, wherein X is selected from the group consisting of Ala and Gly, Y is selected from the group consisting of Ile, Leu, Val, Nle and Met, A has a value from 29-44, and B is NH$_2$, OH or COOH.

BACKGROUND

Prior References—GRF

Human Growth hormone-releasing Factor (hGRF) is a 44 amino acid peptide having growth hormone (GH) releasing activity as reported by Guillemin et al., 218, Science 585 (1982). hGRF is usually isolated from pancreatic human tumor cells (hpGRF). hpGRF has the structure H-Tyr-Ala-Asp-Ala-Ile-Phe-Thr-Asn-Ser-Tyr-Arg-Lys-Val-Leu-Gly-Gln-Leu-Ser-Ala -Arg-Lys-Leu-Leu-Gln-Asp-Ile-Met-Ser-Arg-Gln-Gln-Gly-Glu-Ser-Asn-Gln-Glu-Arg-Gly-Ala-Arg-Ala-Arg-Leu-NH2. Since the initial discovery of hGRF, several peptides, designated herein as analogs, having deleted, substituted or otherwise modified sequences have been reported to have GH releasing activity Rivier et al., 300 Nature 276 (1982) reported a peptide that terminates as a free carboxycylic acid and differs from hGRF by the absence of the C-terminal tetrapeptide amide -Arg-Ala-Arg-Leu-NH$_2$. Rivier et al. tested a number of shortened GRF analogs and reported that, when compared in vitro with the parent hpGRF(1-40)-OH, the following analogs exhibited similar activity: hpGRF(1-29)-NH$_2$, hpGRF(1-32)—NH$_2$, hpGRF(1-39)—NH$_2$, hpGRF(1-40)-NH$_2$, and hpGRF(1-27)-NH$_2$.

Numerous synthetic GRF peptides and GRF analogs have been patented U.S Pat. No. 4,610,976 to Bohlen discloses 44 amino acid synthetic peptides described as extremely potent in stimulating the release of pituitary GH in mammals. These synthetic peptides, biologically active fragments thereof, analogs thereof, or nontoxic salts thereof can be dispersed in a pharmaceutically acceptable carrier and administered for diagnostic or therapeutic purposes. The 44 amino acid polypeptide is believed to be porcine GRF. U.S. Pat. No. 4,605,643 to Bohlen discloses a 44 amino acid synthetic polypeptide that is the replicate of the native GRF of the sheep hypothalamus. The peptide is extremely potent in stimulating the release of GH in mammals. The patent states that the peptide, biologically active fragments thereof, analogs thereof, or nontoxic salts thereof may be administered to animals for therapeutic or diagnostic purposes. As examples of biologically active fragments, Bohlen states that fragments 34-43 residues in length, or even shorter fragments, e.g. oGRF (1-32), that retain an —OH or —NH$_2$ of the C-terminal and retain the desired biological activity are suitable. U.S. Pat. No. 4,595,676 to Spiess discloses the synthesis of rat hypothalamic GRF. A number of polypeptides which have 44 amino acids and are useful in stimulating the release of GH in animals are also disclosed. Reference also is made to biologically active fragments of the polypeptides. U.S. Pat. No. 4,585,756 to Brazeau discloses a 44-residue polypeptide isolated from purified extracts of bovine hypothalami and useful for promoting the growth of animals. Reference is made to biologically active fragments thereof, including bGRF(1-40) and bGRF (1-37) or shorter fragments. U.S. Pat. No. 4,563,352 to Rivier describes the synthesis of human pancreatic GRF and biologically active fragments thereof and provides synthetic peptides useful in stimulating the release of pituitary GH in mammals. U.S. Pat. No. 4,562,175 to Chang discloses a synthetic peptide GRF useful in growth inducing pharmaceutical compositions. The peptide is based on the structure of human pancreatic GRF. The synthetic peptide differs from the natural peptide in that norleucine is substituted for methionine at position 27. Other analogous peptides susceptible to a similar modification also are disclosed, including [D-Ala$^2$, Nle$^{27}$]-hpGRF-(1-44)—NH$_2$ and [D-Ala$^2$, Nle$^{27}$]-ratGRF-(1-43)—NH$_2$). U.S. Pat. No. 4,529,595 to Rivier discloses analogs of hpGRF useful in stimulating the release of pituitary GH in mammals. Biologically active fragments, said to generally extend from the N-terminal to a residue between positions 27 and 32, also are disclosed. U.S. Pat. No. 4,528,190 to Vale provides synthetic polypeptides, useful in stimulating the release of pituitary GH in animals, which have resistance to enzymatic degradation in the body. U.S. Pat. No. 4,518,586 to Rivier describes a 44-amino acid synthetic polypeptide in which any or all of the residues between the 29th and 44th residues may be deleted. U.S. Pat. No. 4,517,181 to Ling discloses synthetic porcine GRF peptides which promote the release of GH by the pituitary gland and teaches that deletions can be made beginning at the carboxyl end of the peptide to create fragments that retain substantial portions of the potency of the peptide. U.S. Pat. No. 4,617,149 discloses a class of 44-amino acid polypeptide analogs of hpGRF bearing substitutions of the amino acid at position 27. Other similar GRF analogs are disclosed in U.S. Pat. Nos. 4,622,312 and 4,626,523.

Similarly, there have been many publications relating to GRF analogs: Ling et al.. Synthesis and In Vitro Bioactivity of C-Terminal Deleted Analogs of Human Growth Hormone-Releasing Factor, *Biochem. Biophys. Res. Commun.*, 123(2), 854-861 (1984); Ling et al., Synthesis and In Vitro Bioactivity Human Growth Hormone-Releasing Factor Analogs Substituted at Position-1, *Biochem. Biophys. Res. Commun.*, 122(1), 304-310 (1984); Wehrenberg et al., In Vitro Biological Potency of Rat and Fragments, *Biochem. Biophys. Res. Commun.*, 115(2), 525-530 (1984); and Lance et al., Super-Active Analogs (1-29)-Amide, *Biochem. Biophys. Res. Commun..* 119(1), 265-272 (1984).

2. Prior References—N-Terminal Modified GRF

Modification of the N-terminal end of GRF and its analogs is known in the art. Hodate et al., *Endocrinol. Japan.* 33:519 (1986) discloses a GRF analog formed by a D-Tyr substitution at the N-Terminal Tyr of native GRF. Frohman *et al., J. Clin. Invest.* 78:906 (1986) discloses GRF analogs which have modifications to the N-terminal end. Frohman suggests that the more active analogs have modifications which increase the protein's resistance to enzymatic degradation at the N-terminus. Similarly, U.S. Pat. No. 4,659,693 discloses a GRF analog in which an N,N'-dialkyl substituted guanidino amino acyl residue is used at position 1 or 2 of the protein.

All the N-terminal modifications in the prior references have been directed to methods for increasing the protein's resistance to enzymatic digestion; the modified proteins are designed to be poor substrates for aminopeptidases and dipeptidylaminopeptidases which would digest the peptide. Such modifications have involved adding D amino acids or chemically modifying the N-terminal end of the protein. None of the prior references discloses adding natural amino acids such as proline to the N-terminal of the protein; such an addition would not be expected to increase resistance to enzymatic attack.

Although numerous patents and publications relating to GRF analogs have been disclosed in the prior art, there exists a continuing need for synthetic GRF analogs which stimulate the release of GH and induce the beneficial effects associated therewith, particularly GRF analogs which are more potent than native GRF.

SUMMARY OF THE INVENTION

It is, therefore, an object of the present invention to provide human growth hormone-releasing factor (hGRF) analogs.

It is another object of the present invention to provide hGRF analogs which stimulate the release of pituitary growth hormone (GH) in animals.

It is another object of the present invention to provide hGRF analogs having an N-terminal modification.

It is another object of the present invention to provide hGRF analogs having the natural amino acid proline added to the N-terminal end of hGRF.

It is a further object of the present invention to provide a composition containing the hGRF analogs of the present invention suitable for administration to animals to stimulate the release of pituitary GH.

It is another object of the present invention to provide a method for using the hGRF analogs of the present invention to stimulate the release of pituitary GH in animals.

These and other objects are achieved by synthesizing hGRF analogs having the sequence [$Pro^0$, $X^{15}$, $Y^{27}$]-hGRF(1-A)-B, wherein X is selected from the group consisting of Ala and Gly, Y is selected from the group consisting of Ile, Leu, Val, Nle and Met, A has a value from 29–44, and B is $NH_2$, OH or COOH, and administering the hGRF analogs to animals to stimulate the release of GH and induce the beneficial effects of increased GH levels.

In the preferred embodiment, hGRF analogs having the sequence [$Pro^0$, $X^{15}$, $Y^{27}$]-hGRF(1-A)-$NH_2$, wherein X is selected from the group consisting of Ala and Gly, Y is selected from the group consisting of Ile, Leu, Val, Nle and Met and A is 29 or 44, are synthesized and administered to animals to stimulate the release of GH and induce the beneficial effects of increased GH levels.

In the most preferred embodiment, an hGRF analog having the sequence [$Pro^0$, $Gly^{15}$, $Met^{27}$]-hGRF(1-44)-$NH_2$ is synthesized and administered to animals to stimulate the release of GH and induce the beneficial effects of increased GH levels. The most preferred structure corresponds to native hGRF having a proline added to the N-Terminal end of the protein.

Other objects, advantages, and novel features of the present invention will become apparent from the following detailed description of the invention.

DETAILED DESCRIPTION OF THE INVENTION

Figure 1:
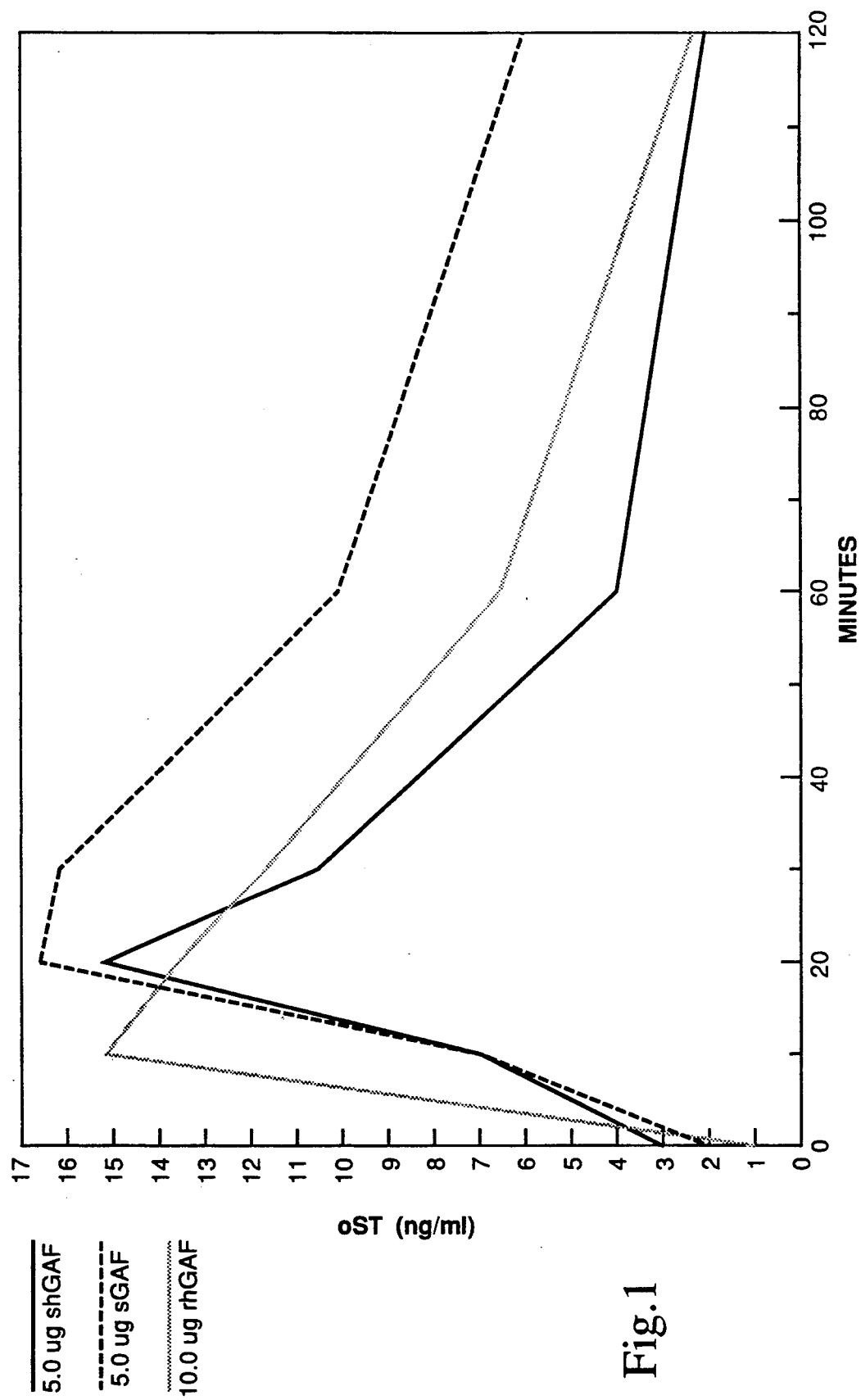
FIG. 1 is a graphic representation showing serum concentrations of ovine somatotropin (oST) versus time for the present GRF analog and native GRF made by recombinant and synthetic techniques.

The amino acids referred to herein are described by shorthand designations as shown in Table 1. All abbreviations used herein for amino acids are three-letter designations unless designated otherwise. Unless designated otherwise, the amino acids used herein are L amino acids.

To simplify the nomenclature used to disclose the peptide sequences of the present invention, the following well-known shorthand notation will be used herein: [$Pro^0$, $X^{15}$, $Y^{27}$]-hGRF(1-A)-B, wherein the (1-A) indicates that the peptide has the same sequence as the first A amino acids of the original 44-residue hGRF; except for the proline added to the N-terminal end of GRF and the optional substitution of Nle for Met at position 27 of the native hGRF For example, [$Pro^0$, $Nle^{27}$]-hGRF(1-31)-$NH_2$ indicates a peptide 31 amino acids long whose sequence is the same as the first 31 amino acids of native hGRF except that Nle has been substituted for Met at position 27 when read from the amino terminal end of native GRF and proline has been added to the N-terminal end of the protein. The complete sequence, expressed using the 3 letter code, for this peptide would therefore be H-Pro-Tyr-Ala-Asn-Ala-Ile-Phe-Thr-Asp-Ser-Tyr-Arg-Lys-Val-Leu-Gly-Gln-Leu-Ser-Ala-Arg -Lys-Leu-Leu-Gln- Asn-Ile-Nle-Ser-Arg-Gln-Gln-$NH_2$. Similarly, [$Pro^0$, $Gly^{15}$, $Met^{27}$]-hGRF(1-44)-$NH_2$ indicates native hGRF having a proline added to the amino terminal end of the protein.

According to the present invention, human growth hormone-releasing factor (hGRF) analogs having the sequence [$Pro^0$, $X^{15}$, $Y^{27}$]-hGRF(1-A)-B, wherein X is selected from the group consisting of Ala and Gly, Y is selected from the group consisting of Ile, Leu, Val, Nle and Met, A has a value from 29–44, and B is $NH_2$, OH or COOH, are synthesized and used to stimulate the release of growth hormone (GH) in animals. The hGRF analogs of the present invention are peptides having the general sequence of hGRF but differing therefrom by (1) the addition of a proline to the N-terminal end of all the hGRF analogs, (2) the deletion of 44 minus A amino acids from the carboxylic terminal end for some of the hGRF analogs, (3) the replacement of the glycine residue at position 15 with Ala for some of the hGRF analogs, (4) the replacement of the methionine residue at position 27 with Nle, Leu, Val or Ile for some of the hGRF analogs, and (5) replacement of $NH_2$ by OH or COOH for some of the hGRF analogs.

Preferably, the hGRF analogs of the present invention have the sequence [$Pro^0$, $X^{15}$, $Y^{27}$]-hGRF(1-A)-$NH_2$, wherein X is selected from the group consisting of Ala and Gly, Y is selected from the group consisting of Ile, Leu, Val, Nle and Met and A is 29 or 44.

Most preferably, the hGRF analogs of the present invention have the sequence [$Pro^0$, $Gly^{15}$, $Met^{27}$]-hGRF-(1-44)-$NH_2$. The sequence for the most preferred hGRF analogs of the present invention is the sequence of native hGRF with a proline added to the N-terminal end of the protein.

Each of the hGRF analogs of the present invention is defined to include pharmaceutically acceptable nontoxic acid addition salts and/or a pharmaceutically acceptable non-toxic carboxylated acid salts.

The term "pharmaceutically acceptable non-toxic acid addition salts" encompasses both organic and inorganic acid addition salts including, for example, those prepared from acids such as hydrochloric, hydrofluoric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. Preferably, the acid addition salts are prepared from hydrochloric acid, acetic acid, or succinic acid. Any of the above salts is prepared by conventional methods well known to skilled artisans.

The term "carboxylated acid salts" includes, for example, ammonium, alkali metal salts such as sodium, potassium, and lithium, and the like.

The hGRF analogs of the present invention can be synthesized by any of a variety of recognized peptide synthesis techniques including classical (solution) methods and solid phase methods, with solid phase synthesis being preferred.

Solid phase techniques in which the C-terminal amino acid of the sequence is attached to an insoluble support followed by sequential addition of the remaining amino acids in the sequence is the preferred method for preparing the hGRF analogs of the present invention. Techniques for solid phase synthesis are described by Barany and Merrifield, Solid-Phase Peptide Synthesis; In "The Peptides: Analysis, Synthesis, Biology. Volume 2: Special Methods in Peptide Synthesis, Part A"; Gross and Meienhofer, J. Eds.; Academic Press: New York, 1980; pp. 3–284: and J. Stewart et al., Solid Phase Peptide Synthesis, 2nd Edition, Pierce Chemical Co., Rockford, IL 1984.

Solid phase synthesis is commenced from the C-terminal end of the peptide by coupling a protected amino acid to a suitable resin. A starting material can be prepared by attaching an amino-protected amino acid via a benzyl ester linkage to a chloromethylated resin or a hydroxymethyl resin or via an amide bond to a benzhydrylamine (BHA) resin or p-methylbenzhydrylamine (MBHA) resin. The resins are available commercially and their preparation is known by one of ordinary skill in the art.

The acid form of peptides may be prepared by the solid phase peptide synthesis procedure using a benzyl ester resin as a solid support. The corresponding amides may be produced by using benzhydrylamine or methylbenzhydrylamine resin as the solid support for solid phase peptide synthesis. Those skilled in the art will recognize that when the BHA or MBHA resin is used, treatment with anhydrous HF to remove the polypeptide from the solid support results in a polypeptide having a terminal amide group.

It should be recognized that the α-amino group of each amino acid employed in the peptide synthesis must be protected during the coupling reaction to prevent side reactions involving the reactive α-amino function. It should also be recognized that certain amino acids contain reactive side-chain functional groups (e.g., sulfhydryl, amino, carboxyl, and hydroxyl), and that such functional groups must also be protected with suitable protecting groups which will prevent a chemical reaction from occurring at that site both during the initial and subsequent coupling steps. Suitable protecting groups, known in the art, are described in E. Gross & J. Meienhofer, The Peptides: Analysis, Synthesis, Biology, Volume 3: Protection of Functional Groups in Peptide Synthesis, Academic Press, New York, N.Y., 1981.

In selecting a particular protecting group, certain conditions must be observed. An α-amino protecting group (1) must render the α-amino function inert under the conditions employed in the coupling reaction, (2) must be readily removable after the coupling reaction under conditions that will not remove side chain protecting groups and will not alter the structure of the peptide fragment, and (3) must eliminate the possibility of racemization upon activation immediately prior to coupling. A side chain protecting group (1) must render the side chain functional group inert under the conditions employed in the coupling reaction, (2) must be stable under the conditions employed in removing the protecting group, and (3) must be readily removable upon completion of the desired amino acid sequence under reaction conditions that will not alter the structure of the peptide chain.

It will be apparent to those skilled in the art that the protecting groups known to be useful for peptide synthesis will vary in reactivity to the agents employed for their removal. For example, certain protecting groups, such as triphenylmethyl and 2-(p-biphenylyl)isopropyloxycarbonyl are very labile and can be cleaved under mild acid conditions. Other protecting groups, such as t-butyloxycarbonyl (Boc), t-amyloxycarbonyl, adamantyloxycarbonyl, and p-methoxybenzyloxycarbonyl, are less labile and require moderately strong acids, such as trifluoroacetic, hydrochloric, or boron trifluoride in acetic acid, for their removal. Still other protecting groups, such as benzyloxycarbonyl (Cbz or Z), halobenzyloxycarbonyl, p-nitrobenzyloxycarbonyl, cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal.

Illustrative examples of amino acid protecting groups include: (1) For an α-amino group, protection may include (a) aromatic urethane-type groups, such as fluorenylmethyloxy-carbonyl (Fmoc), Cbz, and substituted benzyloxycarbonyl, such as, for example, p-chlorobenzyloxycarbonyl, p-bromobenzyloxy-carbonyl, p-nitrobenzyloxycarbonyl, and p-methoxybenzyloxy-carbonyl, o-chlorobenzyloxycarbonyl, 2,4-dichlorobenzyloxy-carbonyl, 2,6-dichlorobenzyloxycarbonyl, and the like; (b) aliphatic urethane-type groups such as Boc, t-amyloxycarbonyl, isopropyloxycarbonyl, 2-(p-biphenylyl)isopropyloxycarbonyl, allyloxycarbonyl, and the like; (c) cycloalkyl urethane-type groups such as cyclopentyloxycarbonyl, cyclohexyloxycarbonyl, cycloheptyloxycarbonyl, adamantyloxycarbonyl, and the like. The preferred amino protecting group is t-butyloxy-carbonyl (Boc).

(2) For the side chain amino group present in Lys, protection may be by any of the groups mentioned hereinabove for protection of an α-amino group. Typical groups include, for example, Boc, p-chlorobenzyloxycarbonyl, p-bromobenzyloxycarbonyl, o-chlorobenzyloxycarbonyl (2-ClZ), 2,6-dichlorobenzyloxycarbonyl, 2,4-dichlorobenzyloxycarbonyl, o-bromobenzyloxycarbonyl, p-nitrobenzyloxycarbonyl t-butyloxycarbonyl, isopropyloxycarbonyl, t-amyloxycarbonyl, cyclopentyloxycarbonyl, cyclohexyloxycarbonyl, cycloheptyloxycarbonyl, adamantyloxycarbonyl, p-toluenesulfonyl, and the like. The preferred side chain amino protecting group is o-chlorobenzyl-oxycarbonyl (2-ClZ).

(3) For the guanidino group of Arg, protection may be by nitro, tosyl (Tos), Cbz, adamantyloxycarbonyl, and Boc. The preferred protecting group is Tos.

(4) For the hydroxyl group of Ser, Thr, or Tyr, protection may be, for example, by $C_1$–$C_4$ alkyl, such as methyl, ethyl, and t-butyl; benzyl (Bzl); substituted benzyl, such as p-methoxybenzyl, p-nitrobenzyl, p-chlorobenzyl, o-chlorobenzyl, and 2,6-dichlorobenzyl. The preferred aliphatic hydroxyl protecting group for Ser and Thr is benzyl (Bzl), while the Tyr aromatic hydroxyl is most commonly protected as the 2,6-dichlorobenzyl ether ($Cl_2$-Bzl).

(5) For the carboxyl group as Asp or Glu, protection may be, for example, by esterification using groups such as benzyl, t-butyl, cyclohexyl, cyclopentyl, and the like. The preferred groups are benzyl (Bzl) and cyclohexyl (cHex).

The amino acids are coupled to the peptide chain using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethyl chloroformate, phenyl chloroformate, sec-butyl chloroformate, isobutyl chloroformate, pivaloyl chloride, or like acid chlorides. Alternatively, the amino acid can be converted to an active ester such as a 2,4,5-trichlorophenyl ester, a pentachlorophenyl ester, a p-nitrophenyl ester, a N-hydroxysuccinimide ester, or an ester formed from 1-hydroxy-benzotriazole.

Another coupling method involves use of a suitable coupling agent such as N,N'-dicyclohexylcarbodiimide (DCC) or N,N'-diisopropylcarbodiimide (DIPCDI). Other appropriate coupling agents, apparent to those skilled in the art, are disclosed in E. Gross & J. Meienhofer, The Peptides: Analysis, Structure, Biology. Vol.1: Major Methods of Peptide Bond Formation, Academic Press, New York, 1979.

The C-terminal amino acid, e.g., Gln, is protected at the N$\alpha$-amino position by an appropriately selected protecting group, in the case of Gln by t-butyloxycarbonyl (Boc). The Boc-Gln-OH can be first coupled to the benzhydrylamine resin using isopropylcarbodiimide at about 25° C. for 2 hours with stirring. Following the coupling of the Boc protected amino acid to the resin support, the $\alpha$-amino protecting group is removed, using trifluoroacetic acid (TFA) in methylene chloride or TFA alone. The deprotection is carried out at a temperature between about 0° C. and room temperature.

After removal of the $\alpha$-amino protecting group, the remaining Boc-protected amino acids are coupled stepwise in the desired order or as an alternative to adding each amino acid separately in the synthesis, some may be coupled to one another prior to addition to the solid phase synthesizer. The selection of an appropriate coupling reagent is known to one of ordinary skill in the art. Particularly suitable is diisopropylcarbodiimide (DIPCDI).

Each protected amino acid or amino acid sequence is introduced into the solid phase reactor in excess, and the coupling may be carried out in a medium of dimethylformamide (DMF) or methylene chloride ($CH_2Cl_2$) or mixtures thereof. In cases where incomplete coupling occurs, the coupling procedure is repeated before removal of the N$\alpha$-amino protecting group prior to the coupling of the next amino acid. The success of the coupling reaction at each stage of synthesis may be monitored. A preferred method of monitoring the synthesis is by the ninhydrin reaction. The coupling reactions can be performed automatically using well-known methods, for example using a Biosearch 9500 Peptide Synthesizer.

Cleavage of the peptide from the resin can be effected using procedures well known in peptide chemistry. Reaction with hydrogen fluoride in the presence of anisole and dimethylsulfide at 0 C. for 1 hour will simultaneously remove the side chain protecting groups and release the peptide from the resin.

Purification of the polypeptides of the invention can be effected using procedures well known in peptide chemistry. The subject polypeptides may be purified using preparative HPLC; however, other known chromatographic procedures well known to skilled artisans such as gel permeation, ion exchange and partition chromatography or countercurrent distribution can also be employed.

The hGRF analogs of the present invention stimulate the release of GH and therefore have many uses. The present compounds may be used, for example, in treating primary dwarfism; short stature; wound healing; bone wasting diseases, such as osteoporosis; general catabolic states due to illness, trauma, or surgery; fracture healing; and the like. In addition, the hGRF analogs of the present invention may be used to promote growth in animals such as cattle, swine, sheep, poultry, and the like.

According to the present invention, a method for stimulating the release of GH in animals comprises administering to the animals an amount of the hGRF analogs of the present invention sufficient to stimulate the release of GH.

The hGRF analogs of the present invention can be administered as the compound or as a pharmaceutically acceptable salt of the compound. The hGRF analogs can be administered alone, in combination, or in combination with pharmaceutically acceptable carriers such as various diluents and vehicles. The carrier can be any biocompatible and hGRF compatible carrier. Most preferably, the hGRF analogs are mixed individually or in combination with pharmaceutically acceptable carriers to form compositions which allow for easy dosage preparation.

Doses of the hGRF analogs are administered to the recipient for a period during which stimulation of the release of GH is desired. The amount of hGRF analog administered may vary depending upon the type of animal, the maturity of the animal, the size of the animal, and whether the dose is to act therapeutically or prophylactically. Generally, the hGRF analogs are administered to the animal according to the present invention in dosages from about 0.05–200 $\mu$g/kg of body weight/day ($\mu$g/kg/day), preferably from about 0.5–100 $\mu$g/kg/day.

The hGRF analogs according to the present invention can be administered to the animals in any acceptable manner including nasally, orally, by injection, using an implant, and the like. Injections and implants are preferred because they permit precise control of the timing and dosage levels used for administration. The hGRF analogs according to the present invention are preferably administered parenterally. As used herein, parenteral administration means administration by intravenous, intramuscular, subcutaneous, or intraperitoneal injection, or by subcutaneous implant.

When administering the hGRF analogs of the present invention parenterally, the pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example glycerol, propylene glycol, liquid polyethylene glycol, and the like), suitable mixtures thereof, and vegetable oils. Proper fluidity can be maintained, for example, by the use of a coating such as lecithin, by the maintenance of the required particle size in the case of dispersion and by the use of surfactants. Nonaqueous vehicles such as cottonseed oil, sesame oil, olive oil, soybean oil, corn oil, sunflower oil, or peanut oil and esters such as isopropyl myristate may also be used as solvent systems for compound compositions. Additionally, various additives which enhance the stability, sterility, and isotonicity of the composition including antimicrobial preservatives, antioxidants, chelating agents, and buffers can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. Any vehicle, diluent, or additive used would, however, have to be compatible with the compounds according to the present invention.

Sterile injectable solutions can be prepared by incorporating the hGRF analogs of the present invention in the required amount of the appropriate solvent with various of the other ingredients, as desired.

The hGRF analogs can be administered to the animals in an injectable formulation containing any biocompatible and compound-compatible carrier such as various vehicles, adjuvants, additives, and diluents.

The hGRF analogs are added to the carrier in amounts sufficient to supply from about 0.05-200 $\mu$g/kg/day to the animal when injected. Preferably, the hGRF analogs are added to the carrier in amounts sufficient to supply from about 0.5-100 $\mu$g/kg/day to the animal.

The hGRF analogs according to the present invention can be administered parenterally to the animals in the form of slow-release subcutaneous implants or targeted delivery systems such as polymer matrices, liposomes, and microspheres. An implant suitable for use in the present invention can take the form of a pellet which slowly dissolves after being implanted or a biocompatible and animal compatible delivery module well known to those skilled in the art. Such well-known dosage forms and modules are designed such that the active ingredients are slowly released over a period of several days to several weeks. Examples of well known implants and modules useful in the present invention micro-infusion pump for dispensing medication at a controlled rate. U.S. Pat. No. 4,486,194 discloses a therapeutic device for administering medicants through the skin. U.S. Pat. No. 4,447,233 discloses a medication infusion pump for delivering medication at a precise infusion rate. U.S. Pat. No. 4,447,224 discloses a variable flow implantable infusion apparatus for continuous drug delivery. U.S. Pat. No. 4,439,196 discloses an osmotic drug delivery system having multi-chamber compartments. U.S. Pat. No. 4,475,196 discloses an osmotic drug delivery system. These patents are incorporated herein by reference. Many other such implants, delivery systems, and modules are well known to those skilled in the art. The implant, pellet, module, or other similar delivery system is designed to deliver the hGRF analogs in amounts from about 0.05-200 $\mu$g/kg/day, preferably from about 0.5-100 $\mu$g/kg/day.

The hGRF analogs according to the present invention can be administered orally to the animal. Conventional methods such as administering the compounds in tablets, suspensions, solutions, emulsions, capsules, powders, syrups, feed compositions, and the like are usable but not preferred since the biological activity of the peptide is often destroyed in the stomach. Known techniques which deliver the peptide orally and retain the biological activity of the peptide are preferred. According to the present invention, one composition for stimulating the release of GH in animals comprises a pharmaceutically acceptable carrier and an amount of an hGRF analog sufficient to stimulate the release of GH admixed with the carrier. The composition of the present invention contains the hGRF analogs in amounts sufficient to supply from about 0.05-200 $\mu$g/kg of body weight/day ($\mu$g/kg/day), preferably from about 0.5-100 $\mu$g/kg/day.

The composition can be in a form suitable for parenteral administration, typically suspensions, solutions, emulsions, injectable formulations, implants, and the like.

The hGRF analogs according to the present invention can be administered to the animals in a composition comprising an implant or injectable formulation containing any biocompatible and hGRF analog-compatible carrier such as various vehicles, adjuvants, additives, and diluents.

Preferably, the composition according to the present invention is (1) an implant pellet comprising a biocompatible and hGRF analogs-compatible implant material and an amount of the hGRF analog sufficient to stimulate the release of GH, or (2) an injectable formulation comprising a biocompatible and hGRF analogs-compatible carrier and an amount of the hGRF analog sufficient to stimulate the release of GH.

It is especially advantageous to formulate the hGRF analogs of the present invention in unit dosage form for ease of administration and uniformity of dosage. Unit dosage form as used herein refers to physically discrete units suited as unitary dosages for the subject to be treated. Each unit contains a predetermined quantity of the compound calculated to produce the desired therapeutic effect in association with the pharmaceutically acceptable carrier. The specific unit dosage form is dictated by and directly dependent upon (a) the unique characteristics of the particular composition and (b) the particular therapeutic or prophylactic effect to be achieved.

Any animal species in need of prophylactic or therapeutic treatment using GH can be administered the hGRF analogs and compositions according to the present invention. Human, bovine, porcine, canine, feline, equine, avian, and ovine are preferred, with livestock and poultry such as cattle, swine, sheep, chickens, and turkeys being most preferred.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

Preparation of [Pro$^0$, Gly$^{15}$, Met$^{27}$]-hGRF(1-44)-NH$_2$

[Pro$^0$, Gly$^{15}$, Met$^{27}$]-hGRF(1-44)-NH$_2$ was synthesized by BaChem Bioscience in Philadelphia, PA at our request. The peptide was synthesized by sequential coupling of amino acids using BOC-amino acid solid phase synthesis on a PAM resin using a Labor-Tech SP640 peptide synthesizer. The peptide was purified on a Waters Delta Prep column using an acetonitrile gradient in 0.1% TFA.

EXAMPLE 2

The [Pro$^0$, Met$^{27}$]-hGRF(1-44)-NH$_2$ synthesized in Example 1 was tested for purity by HPLC using a Bakerbond wide-pore C18 column. The column was eluted using an acetonitrile gradient in TEAP (15% acetonitrile for 2 minutes and then a linear gradient up to 60% acetonitrile at 45 minutes). The flow rate was 1.0 ml/minute and the column was monitored by UV absorbance at 220 nm (0.5 absorbance units full-scale).

Analysis of the HPLC chromatogram revealed only a single dominant peak was found which eluted at 18.52 minutes thus indicating that only the [Pro$^0$, Gly$^{15}$, Met$^{27}$]-hGRF-(1-44)-NH$_2$ was in the sample tested.

EXAMPLE 3

Approximately 1 nmol of the [Pro$^0$, Gly$^{15}$, Met$^{27}$]-nGRF(1-44)-NH$_2$ synthesized in Example 1 was tested for amino acid sequence and content. The compound was dissolved in 0.1% trifluoroacetic acid and applied directly on an Applied Biosystems 477A protein sequencer. The sequence was called through the first 44 residues and the predicted sequence was obtained. The amino acid analysis was performed on a Beckman 121MB Amino Acid Analyzer. The data obtained were consistent with the predicted sequence for [Pro$^0$, Gly$^{15}$, Met$^{27}$]-hGRF-(1-44)-NH$_2$.

EXAMPLE 4

Whether lambs (40-45 kg) were injected subcutaneously with the following GRF compounds in a phosphate buffered saline vehicle (pH 7):
10.0 ug/kg recombinant native hGRF (rhGRF)
5.0 ug/kg synthetic native hGRF (shGRF)
5.0 ug/kg [Pro$^0$, Gly$^{15}$, Met$^{27}$]-hGRF(1-44)-NH$_2$ (aGRF)

There were 4 animals per treatment group and each treatment was repeated 3 times to give a total of 12 samples/time point/treatment. The animals were bled at time 0, 10, 20, 30, 60 and 120 minutes after injection and analyzed for serum ovine somatotropin (oST) by radioimmunoassay (RIA). The results are shown in FIG. 1.

Referring to FIG. 1, at 120 minutes post injection, the [Pro$^0$, Gly$^{15}$, Met$^{27}$]-hGRF(1-44)-NH$_2$ analog gave oST concentrations greater than those at time 0 whereas the native synthetic hGRF treated animals had returned to baseline serum oST levels. This shows that [Pro$^0$, Gly$^{15}$, Met$^{27}$]-hGRF(1-44)-NH$_2$ has prolonged in vivo biological activity; although uncertain as to the exact mechanism, this prolonged activity is likely due to a decreased clearance rate for aGRF.

EXAMPLE 5

Example 4 was repeated using the following treatments:
20.0 ug/kg recombinant native hGRF (rhGRF)
10.0 ug/kg synthetic native hGRF (shGRF)
10.0 ug/kg [Pro$^0$, Gly$^{15}$, Met$^{27}$]-hGRF(1-44)-NH$_2$ (aGRF)

Figure 2:
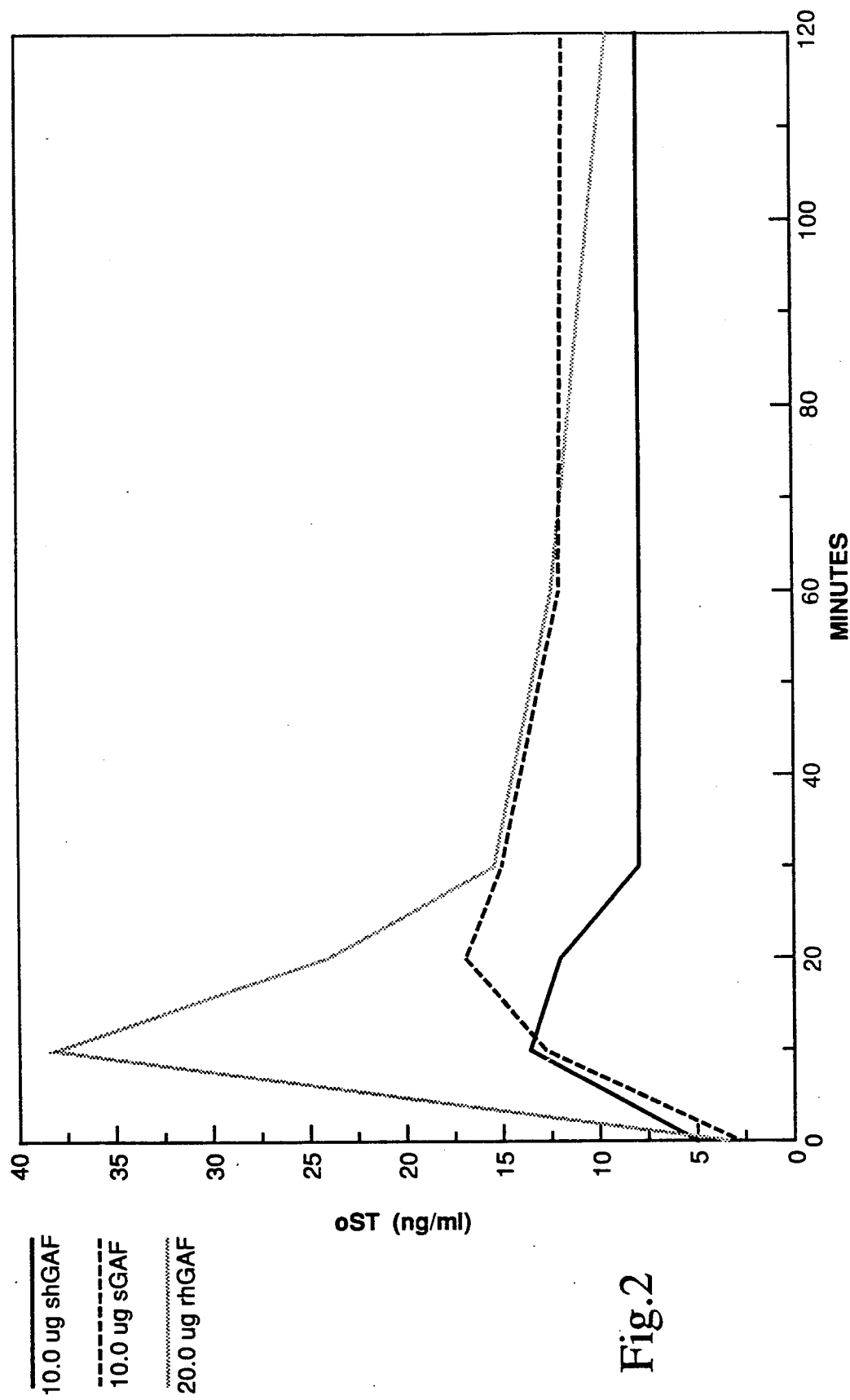
FIG. 2 is a graphic representation showing serum concentrations of ovine somatotropin (oST) versus time for the present GRF analog and native GRF made by recombinant and synthetic techniques.

Serum profiles after the injections are shown in FIG. 2.

Referring to FIG. 2, at 120 minutes post injection, the [Pro$^0$, Gly$^{15}$, Met$^{27}$]-hGRF(1-44)-NH$_2$ analog gave oST concentrations greater than those at time 0 whereas the native synthetic hGRF treated animals had returned to baseline serum oST levels. This again shows that the [Pro$^0$, Gly$^{15}$, Met$^{27}$]-hGRF(1-44)-NH$_2$ analog has prolonged in vivo bioactivity compared to native GRF.

Obviously many modifications and variations of the present invention are possible in light of the above teachings. It is therefore to be understood that within the scope of the appended claims the invention may be practiced otherwise than as specifically described.

TABLE 1

| Amino Acid Nomenclature | | |
|---|---|---|
| Name | 3-letter | 1-letter |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met(O) | — |
| Methionine methylsulfonium | Met(S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

What is claimed is:

1. Human Growth Hormone-Releasing Factor (hGRF) analogs having the sequence [Pro$^0$, X$^{15}$, Y$^{27}$]-hGRF(1-A)-B, wherein X is selected from the group consisting of Ala and Gly, Y is selected from the group consisting of Ile, Leu, Val, Nle and Met, A has a value from 29-44, and B is NH$_2$, OH or COOH.

2. The hGRF analogs of claim 1 wherein B is NH$_2$.

3. The hGRF analogs of claim 2 wherein X is Gly.

4. The hGRF analogs of claim 3 wherein Y is Met.

5. The hGRF analogs of claim 4 wherein A is 44.

6. A method for stimulating the release of growth hormone (GH) in an animal, comprising:
administering to said animal an amount of human growth hormone-releasing factor (hGRF) analogs sufficient to stimulate the release of growth hormone (GH), the hGRF analogs having the sequence [Pro$^0$, X$^{15}$, Y$^{27}$]-hGRF-(1-A)-B, wherein X is selected from the group consisting of Ala and Gly, Y is selected from the group consisting of Ile, Leu, Val, Nle and Met, A has a value from 29–44, and B is $NH_2$, OH or COOH.

7. The method of claim 6 wherein B is $NH_2$.

8. The method of claim 7 wherein X is Gly.

9. The method of claim 8 wherein Y is Met.

10. The method of claim 9 wherein A is 44.

11. The method of claim 6 wherein the hGRF analog is administered in dosages of from about 0.05–200 µg/kg of body weight/day.

12. The method of claim 6 wherein the hGRF analog is administered parenterally.

13. The method of claim 12 wherein the hGRF analog is administered using an implant, said implant further comprising:
   a biocompatible and the hGRF analog compatible implant material; and
   an amount of the hGRF analog sufficient to stimulate the release of GH.

14. The method of claim 12 wherein the hGRF analog is administered in an injectable formulation, said injectable formulation further comprising:
   a biocompatible and the hGRF analog compatible carrier; and
   an amount of the hGRF analog sufficient to stimulate the release of GH.

15. The method of claim 6 wherein said animal is selected from the group consisting of cattle and sheep.

16. A composition for stimulating the release of growth hormone (GH) in an animal, comprising:
   a pharmaceutically acceptable carrier; and
   an amount of a human growth hormone-releasing factor (hGRF) analog sufficient to stimulate the release of GH, the hGRF analogs having the sequence $[Pro^0, X^{15}, Y^{27}]$-hGRF(1-A)-B, wherein X is selected from the group consisting of Ala and Gly, Y is selected from the group consisting of Ile, Leu, Val, Nle and Met, A has a value from 29–44, and B is $NH_2$, OH or COOH.

17. The composition of claim 16 wherein B is $NH_2$.

18. The composition of claim 17 wherein X is Gly.

19. The composition of claim 18 wherein Y is Met.

20. The composition of claim 19 wherein A is 44.

21. The composition of claim 16 containing the hGRF analog in dosages of from about 0.05–200 µg/kg of body weight/day.

22. An implant composition comprising a composition in accordance with claim 16 and a biocompatible implant material wherein said biocompatible implant material also is compatible with said hGRF analog.

23. An injectable composition comprising a composition in accordance with claim 16 wherein said pharmaceutically acceptable carrier includes a sterile aqueous solution.

* * * * *

UNITED STATES PATENT AND TRADEMARK OFFICE
CERTIFICATE OF CORRECTION

PATENT NO. : 5,137,872

DATED : August 11, 1992

INVENTOR(S) : Seely, et al.

It is certified that error appears in the above-identified patent and that said Letters Patent is hereby corrected as shown below:

Column 1, line 6, "hormonereleasing" should read --hormone releasing--

Column 1, line 27, "activity" should read --activity.--

Column 1, line 39, "patented" should read --patented:--

Column 4, line 33, "Nle" should read --Nle--

Column 9, line 63, before the word micro-fusion, insert --include: U.S. Patent No. 4,487,603 discloses an implantable--

Column 11, line 21, "[Pro$^0$, Met$^{27}$]" should read --[Pro$^0$, Gly$^{15}$, Met$^{27}$]--

Column 11, line 36, "nGRF" should read --hGRF--

Column 11, line 48, "Whether" should read --Wether--

Signed and Sealed this

Twenty-first Day of September, 1993

Attest:

BRUCE LEHMAN

*Attesting Officer*   *Commissioner of Patents and Trademarks*